United States Patent
Chang et al.

(10) Patent No.: US 11,452,864 B2
(45) Date of Patent: Sep. 27, 2022

(54) METHOD AND SYSTEM FOR TREATING NEURAL DISORDERS

(71) Applicants: BIOPRO SCIENTIFIC CO., LTD., Hsinchu (TW); NATIONAL TSING HUA UNIVERSITY, Hsinchu (TW)

(72) Inventors: Pin Chang, Hsinchu (TW); Hsin Chen, Hsinchu (TW); Yen-Chung Chang, Hsinchu (TW); Shih-Rung Yeh, Hsinchu (TW)

(73) Assignees: BIOPRO SCIENTIFIC CO., LTD., Hsinchu (TW); NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/877,495

(22) Filed: May 19, 2020

(65) Prior Publication Data
US 2020/0368522 A1 Nov. 26, 2020

Related U.S. Application Data

(60) Provisional application No. 62/850,331, filed on May 20, 2019.

(51) Int. Cl.
*A61N 1/05* (2006.01)
*A61N 1/36* (2006.01)

(52) U.S. Cl.
CPC .......... *A61N 1/0534* (2013.01); *A61N 1/361* (2013.01); *A61N 1/36064* (2013.01);
(Continued)

(58) Field of Classification Search
CPC .............. A61N 1/0534; A61N 1/36064; A61N 1/36067; A61N 1/36075; A61N 1/36096;
(Continued)

(56) References Cited

U.S. PATENT DOCUMENTS 6,066,163 A 5/2000 John
6,176,242 B1 * 1/2001 Rise .................. A61M 5/14276
128/898

(Continued)

FOREIGN PATENT DOCUMENTS

WO 2006053114 5/2006
WO 2017181068 10/2017

OTHER PUBLICATIONS

Extended European Search Report of the EP family application EP20175358.9 dated Oct. 29, 2020.
(Continued)

*Primary Examiner* — Tammie K Marlen
(74) *Attorney, Agent, or Firm* — WPAT, P.C., Intellectual Property Attorneys; Anthony King

(57) ABSTRACT

A method for treating neural disorders is provided. The method includes the following operation. A stimulation is delivered to a layer of a cortex of a patient with a neural disorder, wherein the stimulation is delivered to less than all layers of the cortex of the patient. In another method for treating neural disorders, a stimulation is delivered to a cortex of a patient with a neural disorder, wherein the stimulation delivered to one of a plurality of layers of the cortex is stronger than to other layers of the cortex. The system for treating neural disorder is also provided. The system includes a stimulation signal generator and a layer-specific stimulation means. The layer-specific stimulation means is coupled to the stimulation signal generator, configured to deliver a stimulation to a specific layer of a cortex of a patient with a neural disorder.

13 Claims, 9 Drawing Sheets

(52) U.S. Cl.
CPC ..... *A61N 1/36067* (2013.01); *A61N 1/36075* (2013.01); *A61N 1/36096* (2013.01)

(58) Field of Classification Search
CPC ................ A61N 1/361; A61N 1/36071; A61N 1/36082; A61N 1/0531
See application file for complete search history.

(56) References Cited

U.S. PATENT DOCUMENTS

| | | |
|---|---|---|
| 6,484,059 B2 | 11/2002 | Gielen |
| 7,236,830 B2 | 6/2007 | Gliner |
| 7,269,456 B2 | 9/2007 | Collura |
| 7,616,998 B2 | 11/2009 | Nuttin et al. |
| 7,979,129 B2 | 7/2011 | Gill |
| 8,676,327 B2 | 3/2014 | Doerr et al. |
| 8,903,499 B2 | 12/2014 | Pless et al. |
| 8,923,977 B2 | 12/2014 | Decre et al. |
| 8,948,875 B2 | 2/2015 | Paulus et al. |
| 9,014,820 B2 | 4/2015 | Lee et al. |
| 9,949,376 B2 | 4/2018 | Greenberg et al. |
| 2006/0106430 A1* | 5/2006 | Fowler ............... A61N 1/36082 607/45 |
| 2011/0171325 A1* | 7/2011 | Lozano ................ A61N 1/0531 424/722 |
| 2019/0099609 A1* | 4/2019 | Lee ........................ A61N 2/006 |

OTHER PUBLICATIONS

Ki Yong Kwon et al., "Integrated Slanted Microneedle-LED Array for Optogenetics", 2013 35th Annual International Conference of the IEEE Engineering in Medicine and Biology Society (EMBC), Osaka, 2013, pp. 249-252.

\* cited by examiner

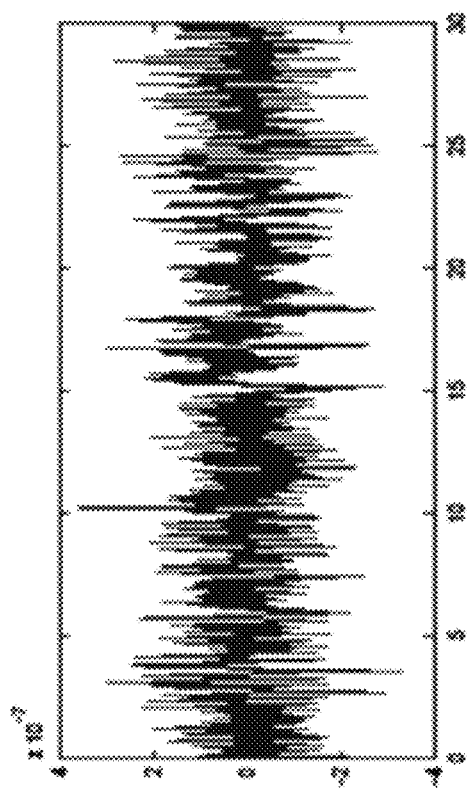
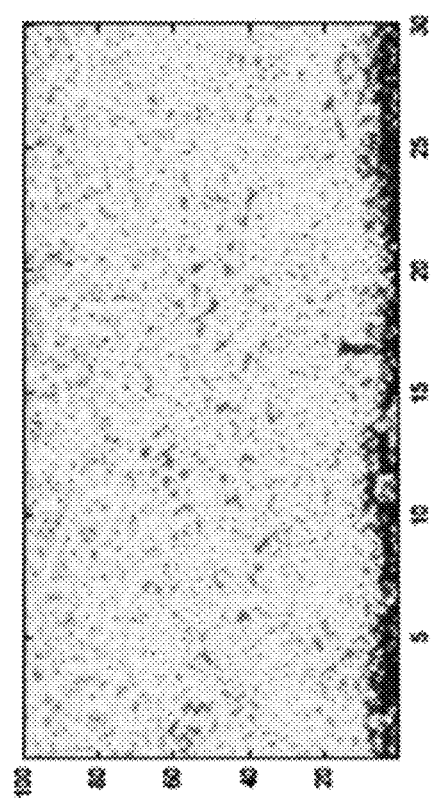
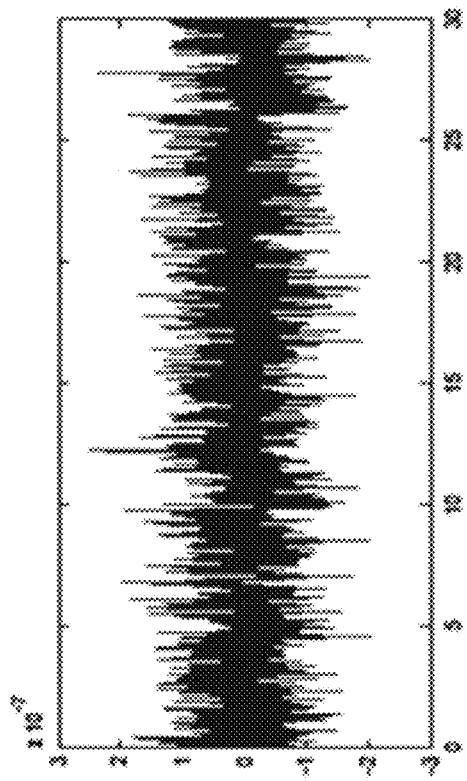
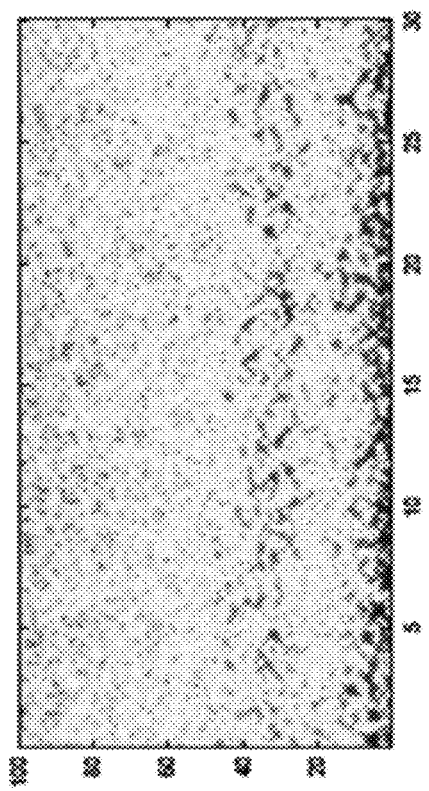
Fig. 4A
Fig. 4B

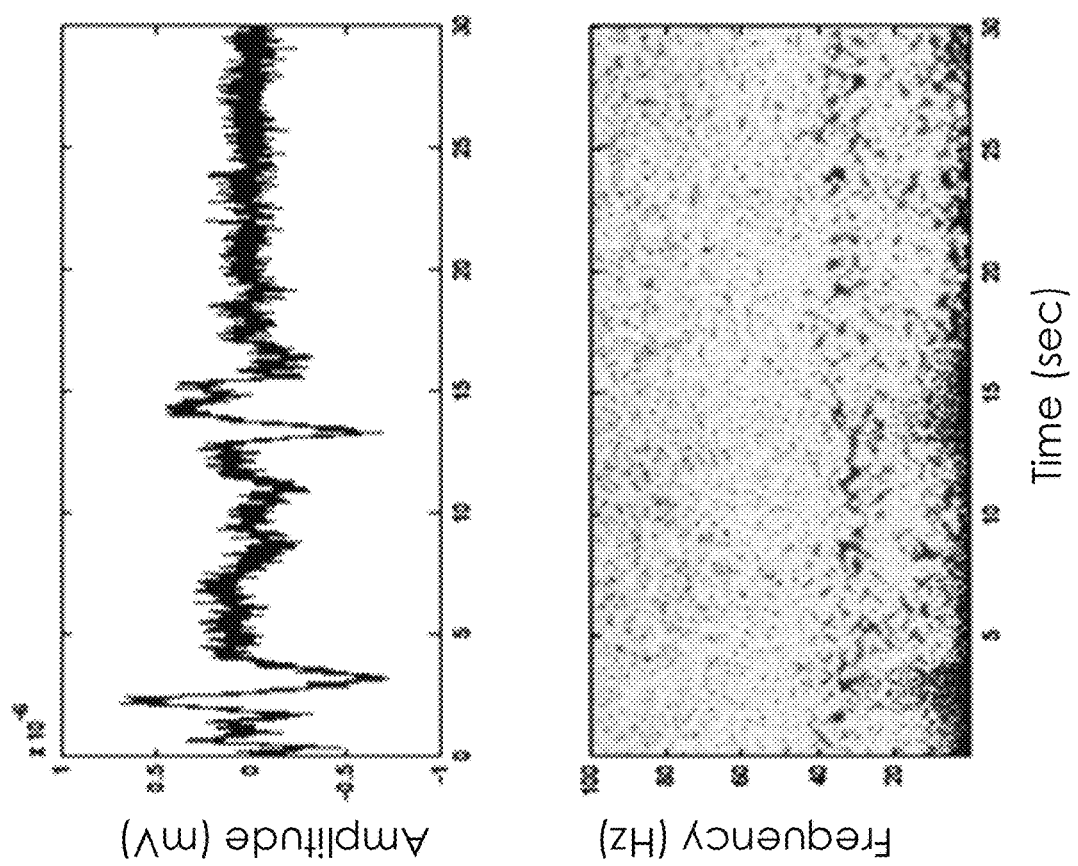

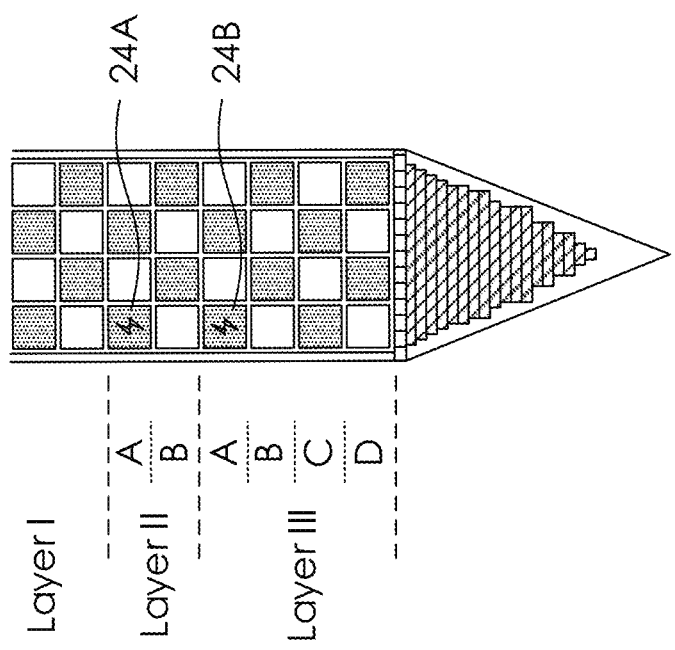

METHOD AND SYSTEM FOR TREATING NEURAL DISORDERS

CROSS REFERENCE TO RELATED APPLICATION

This application claims the benefit of prior-filed U.S. provisional application No. 62/850,331, filed on May 20, 2019, and incorporates its entirety herein.

FIELD

The present disclosure relates to a method for treating neural disorders, particularly, to a method that stimulates the cortex at a layer level.

BACKGROUND

Parkinson's disease (PD) is a kind of movement disorder which replaces the patient's normal movement to tremor, rigidity and stiffness. In order to treat neural disorders such as Parkinson's disease, deep brain stimulation (DBS) has been researched and practiced worldwide. This surgical procedure involves implanting electrodes within several deep areas of brain such as subthalamic nucleus (STN) or globus pallidus (GPi), which are about 8 cm below dura. These implanted electrodes produce electrical impulses that regulate abnormal impulses in patient's brain, and thus releasing Parkinson's disease symptoms.

However, DBS procedure is highly invasive due to the location and the size of STN. STN is a lens-shaped nucleus whose location in the brain is variable among individuals but generally is about 8 cm in depth below dura, and the section length for contacting stimulation lead is only about 4 mm, therefore, the precise navigation for implanting the DBS electrode to STN is challenging. Moreover, important brain tissues and blood vessels can be on the path of the deep brain implantation, and thus chances of temporarily or permanently damaging such brain tissues and blood vessels are considerably high. In other words, the risk of complication of such deep brain surgical procedure is high to an extent that seeking a lower risk alternative can be of an urgent need.

BRIEF DESCRIPTION OF THE DRAWINGS

Aspects of the present disclosure are best understood from the following detailed description when read with the accompanying figures. It is noted that, in accordance with the standard practice in the industry, various structures are not drawn to scale. In fact, the dimensions of the various structures may be arbitrarily increased or reduced for clarity of discussion.

FIG. 4A illustrates the beta oscillations are detected according to the brainwave of a rat with Parkinson's disease according to some embodiments of the present disclosure.

FIG. 4B illustrates the beta oscillations are suppressed by stimulating at Layer II and Layer III of the cortex according to some embodiments of the present disclosure.

FIG. 4C illustrates the beta oscillations are detected according to the brainwave of a rat with Parkinson's disease according to some embodiments of the present disclosure.

FIG. 7 illustrates the system for treating neural disorders according to some embodiments of the present disclosure.

DETAILED DESCRIPTION

Figure 1:
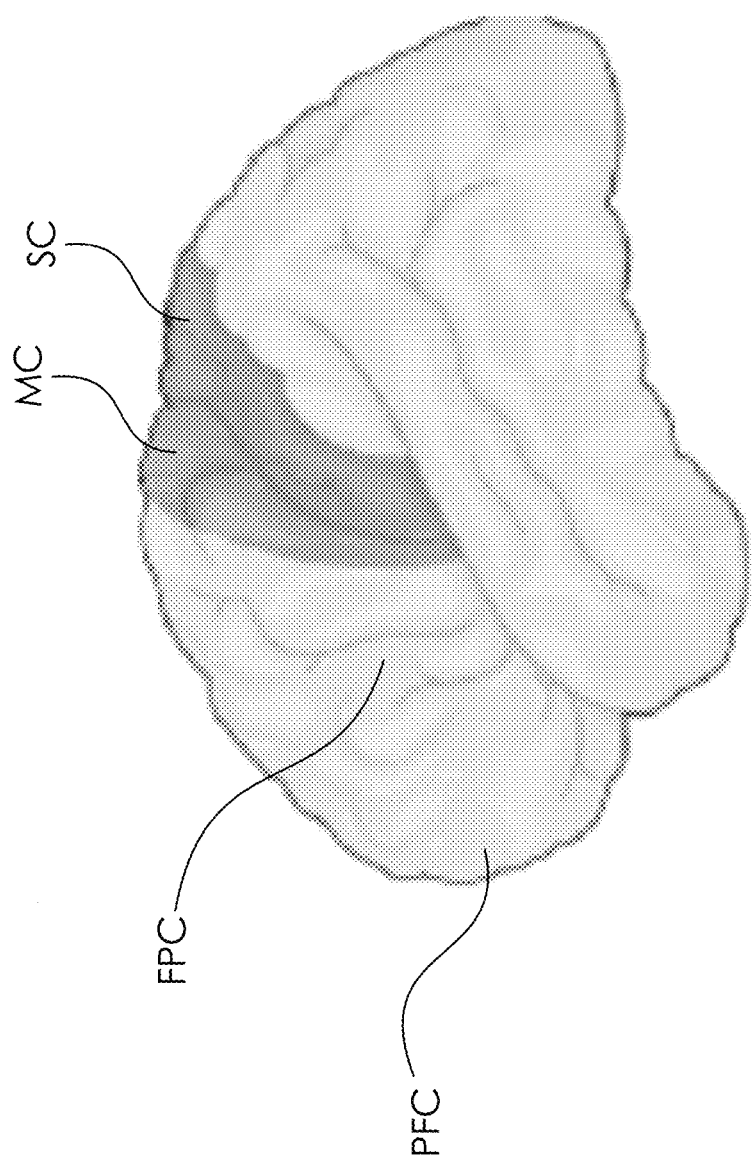
FIG. 1 illustrates the positions of the somatosensory cortex and the motor cortex according to some embodiments of the present disclosure.

The following disclosure provides many different embodiments, or examples, for implementing different features of the provided subject matter. Specific examples of elements and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper", "on" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

As used herein, the terms such as "first", "second" and "third" describe various elements, components, regions, layers and/or sections, these elements, components, regions, layers and/or sections should not be limited by these terms. These terms may be only used to distinguish one element, component, region, layer or section from another. The terms such as "first", "second", and "third" when used herein do not imply a sequence or order unless clearly indicated by the context.

The present disclosure provides a method for treating neural disorders including Parkinson's disease and some movement disorder syndromes such as bradykinesia, dystonia, rigidity, gait disorders, and essential tremor. In some embodiments, the present disclosure may be further applied to other disease or dysfunctions such as Alzheimer's disease (AD), epilepsy, stroke, traumatic brain injury (TBI), pain, coma, paralysis, Tourette syndrome, tinnitus, depression, obsessive-compulsive disorder (OCD), or headache.

In some embodiments, the method stimulates the cerebral cortex (hereinafter cortex) for treating neural disorders. The cortex is a thin membrane of the brain which composed of several layers that covers the outer portion (about 1.5 mm to about 5 mm) of the cerebrum. It is covered by the meninges and often referred to as gray matter. The cortex is gray because nerves in this area lack the insulation that makes most other parts of the brain appear to be white.

The cortex is involved in several functions of the body, including determining intelligence, determining personality, motor function, planning and organization, touch sensation, processing sensory information, and language processing. The cortex may be divided into a couple of areas based on the functions such as somatosensory cortex and the motor cortex. For example, the somatosensory cortex may receive input from the thalamus and process information related to the senses. To be more detailed, in some classification, the cortex further includes the visual cortex of the occipital lobe, the auditory cortex of the temporal lobe, and the gustatory cortex.

In some embodiments, the area of the cortex be stimulated in the present disclosure is the somatosensory cortex, the motor cortex, or the combinations thereof. More specifically, the cortex mentioned in the present disclosure is the neocortex which commands higher functions of mammals, such as sensory perception, generation of motor commands, emotion, and cognition. The neocortex includes areas involving in motor, primary visual, somatosensory, and auditory functions. Referring to FIG. 1, where two of the neocortex areas are adequate to stimulate to treat neural disorders as aforementioned: the motor cortex MC and the somatosensory cortex SC.

Furthermore, it is also available for relieving pain or treating other disorders related to brain dysfunctions by delivering stimulations to at least a layer of cortex. For instance, stimulating a layer of motor cortex for relieving central pain syndrome, stimulating a layer of prefrontal cortex (PFC) for recovering self-control ability in obesity syndrome, stimulating a layer of motor cortex, dorsomedial prefrontal cortex (DMPFC) or frontopolar cortex (FPC) for improving major depressive disorder, and stimulating a layer of dorsolateral prefrontal cortex (DLPFC) for treating substance use disorder (SUD) or drug use disorder.

In some embodiments, in the method for treating Parkinson's disease, beta oscillation (20-40 Hz) is a pathological signature relating to Parkinson's disease. The motor cortex controls voluntary movement of body parts and it is where the beta oscillations are detected strongly and clearly in brainwave. Moreover, beta oscillation is not only being greatly enhanced in Parkinson's disease but also the beta activity at rest and beta changes in response to treatment with parkinsonian syndromes. The somatosensory cortex processes information received from body, and the beta oscillations are also significantly detected in such region.

Figure 2:
FIG. 2 illustrates the layers of the cortex according to some embodiments of the present disclosure.

Referring to FIG. 2, regardless of the functional areas, the cortex can be divided into at least 6 layers, including Layer I, Layer II, Layer III, Layer IV, Layer V and Layer VI from superficial to deep. Each layer contains different neuronal shapes, sizes and density as well as different organizations of nerve fibers 30. As a result, different zones of each neuron such as the receptive zone and the output zone, may position in different layers of the cortex. Accordingly, the stimulation delivered to different layers of the cortex may trigger different neurons to act and result in various feedbacks.

In some embodiments, the method targets the cortex to be stimulated at a layer level, including the external granular layer (approximately 0.09-0.19 mm), the external pyramidal layer (approximately 0.45-1.2 mm), and the internal pyramidal layer (approximately 0.25-0.61 mm), which are usually numbered as Layer II, Layer III, and Layer V of the cortex respectively.

To improve the treatment under the approach of suppressing the beta oscillations, some embodiments of the present disclosure deliver the stimulation from an implanted electrical signal generator to the layers of cortex instead of the deep brain. Not only the Layer II, Layer III, Layer V, or combinations thereof as aforementioned, in some embodiments, stimulation may also be delivered, independently, simultaneously or sequentially, to other layers of the cortex, for example, molecular layer (Layer I, approximately 0.15-0.23 mm), internal granular layer, (Layer IV, approximately 0.10-0.36 mm), and polymorphic layer (Layer VI, approximately 0.35-1.15 mm), while stimulating any of the Layer II, Layer III, Layer V, and combinations thereof.

By stimulating the cortex at a layer level thereof, not only the stimulation lead may be navigated to the target layer easier, but also the aforesaid risk associated with deep brain surgery can be decreased because implanting the electrical signal generator to the cortex, or hereinafter shallow brain implantation, may cause limited interferences with neurons, brain tissues, and blood vessels. In other words, the present disclosure may provide a less invasive alternative to the DBS treatment while effectively inhibiting/suppressing beta oscillations.

In some embodiments of the present disclosure, prior to delivering the stimulation to a layer of the cortex of a patient with neural disorder, a stimulation lead may be implanted to the cortex. In some embodiments, the stimulation lead includes an electrode at a distal end of the stimulation lead. In some embodiments, a length of the stimulation lead is corresponding to a depth of the layer of the cortex. In some embodiments, the stimulation lead is electrically coupled to the electrical signal generator.

The electrode of the electrical signal generator can be positioned to be in proximity to one or more specific layers of the cortex. For example, one electrode on the stimulation lead can be in proximity to, adjacent to, or in an effective distance to Layer I, Layer II, or Layer V of the cortex. For example, a plurality of electrodes are positioned on the stimulation lead. The electrodes can be in proximity to, adjacent to, or in an effective distance to Layer I, Layer II, and Layer V of the cortex. In some embodiments, the electrodes are in contact within the layer(s) of the cortex.

In some embodiments, more than one of the electrodes on the stimulation lead may stimulate the layers of the cortex concurrently, and the electrodes delivering stimulations do not need to be adjusted. Accordingly, in some embodiments, the electrodes may deliver the stimulation to at least two nonadjacent layers of the cortex concurrently.

In some other embodiments, prior to delivering the stimulation to a layer of the cortex of a patient with neural disorder, no stimulation lead is implanted to the cortex. Instead, the stimulation may be delivered by injecting gamma-amino butyric acid receptor antagonist to the layer of the cortex.

In some embodiment, prior to delivering the stimulation to a layer of the cortex of a patient with neural disorder, no stimulation lead is implanted to the cortex. Instead, the stimulation may be delivered by a stimulation receptor in the specific layer of the cortex. In some embodiments, the stimulation receptor may be a light-sensitive receptor such as an optogenetics actuator. Optogenetics is a method for controlling a neuron's activity using light and genetic engineering, more precisely, the light may control neurons that have been genetically modified to express light-sensitive ion channels. In some examples, the optogenetics actuator may be channelrhodopsin, halorhodopsin, archaerhodopsin, etc., and the stimulation within the layers of cortex may be evoked by the optogenetics actuators, which can be controlled by a light source outside of the patient's body as a non-invasive stimulation means.

In some embodiments, prior to delivering the stimulation to a layer of the cortex of a patient with neural disorder, no stimulation lead is implanted to the cortex. Instead, an ultrasonic receptor such as an ultrasonic transducer, a magnetic bead, or a radio frequency receptor, each of the aforesaid non-invasive receptors is configured to evoke the stimulation in the specific layer(s) of the cortex by associated energy sources (i.e., ultrasonic waves, magnetic field, or radio frequency waves). For instance, one or more ferrite beads may be implanted to at least one of the specific layers of the cortex and be controlled extracranially. In some embodiments, the technique of Transcranial Magnetic Stimulation (TMS) may be applied. TMS is a non-invasive approach for brain stimulation which may change a magnetic field for inducing an electric current at a specific area of the brain based on electromagnetic induction. In such embodiments, a stimulation signal generator such as a magnetic controller which may include an electric pulse generator and a magnetic coil connected to the scalp of a patient, and the magnetic controller may generate a changing electric current within the magnetic coil, which induces a magnetic field, and the magnetic field may cause a second inductance of inverted electric charge within the brain. Accordingly, by controlling the strength and direction of the induced magnetic field, the specific layers of cortex implanted with ferrite beads may be stimulated by the inverted electric charge selectively and accurately.

In some embodiments, prior to delivering the stimulation to a layer of the cortex of a patient with neural disorder, no stimulation lead is implanted to the cortex. Instead, a plurality of nano particles may be implanted or injected to at least a specific layer of the cortex as receptors. In such embodiments, the nano particles within the specific layers of the cortex may be trapped, oriented or transported by ultrasonic waves provided by the stimulation signal generator such as an ultrasonic transducer extracranially, and the movement of the nano particles may be a form of stimulation to the specific layers of the cortex. The nano particles may include various types of materials and components, and they also may be carried into human body by genetically modified biological vessels.

In some embodiments, prior to delivering the stimulation to a layer of the cortex of a patient with neural disorder, no stimulation lead is implanted to the cortex. Instead, the receptor responsive to radio frequency may be delivered to the specific layers of the cortex. The stimulation signal generator may be an electrical signal generator generating radio frequency wave so that it may be affect the behavior of the radio frequency receptors and evoke the stimulation extracranially.

Figure 3A:
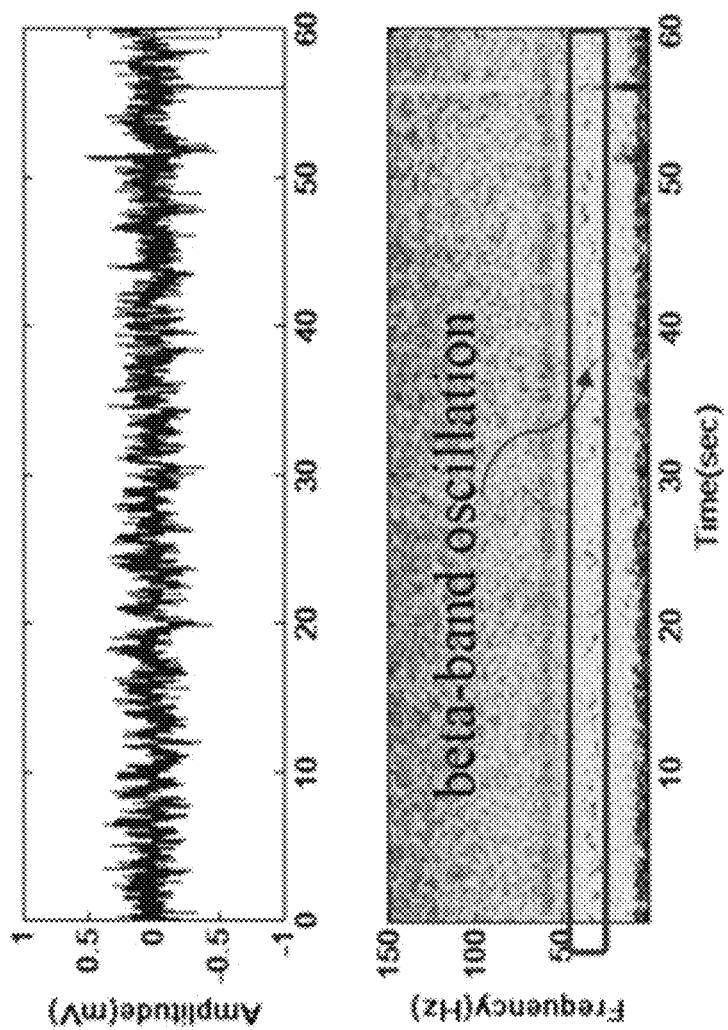
FIG. 3A illustrates the energy of beta signals are greatly enhanced in rats with Parkinson's disease according to some embodiments of the present disclosure.
Figure 3B:
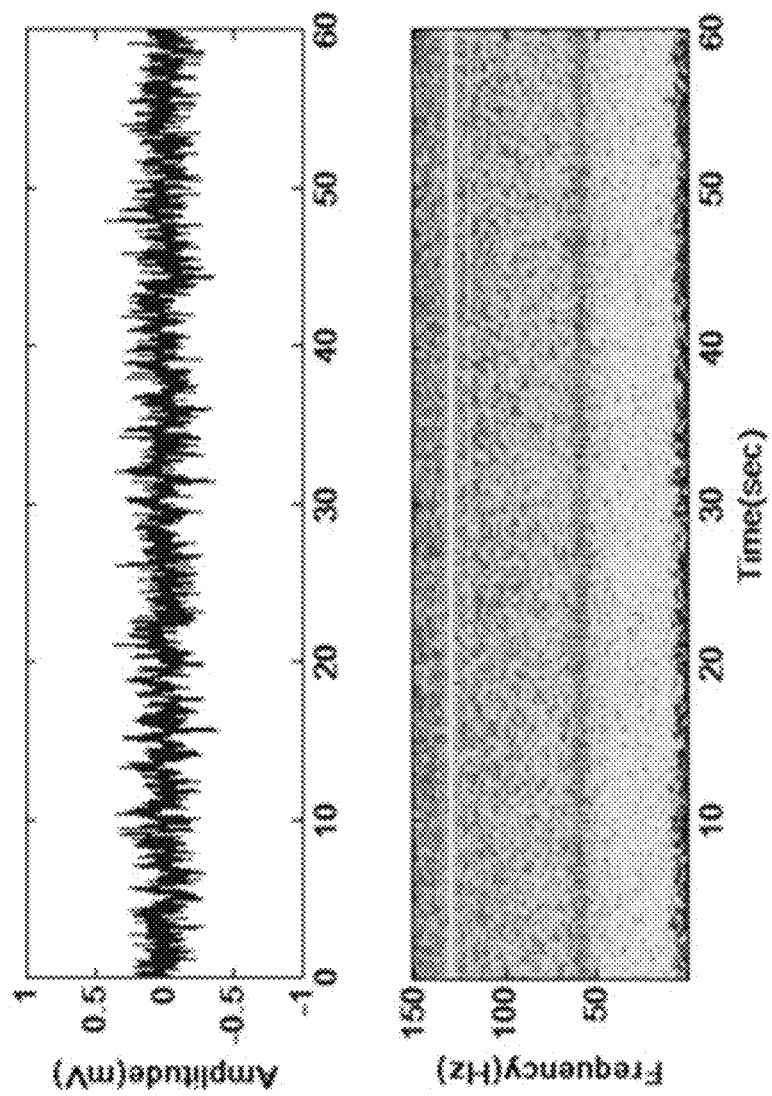
FIG. 3B illustrates the beta oscillations are suppressed by stimulating STN according to some embodiments of the present disclosure.

As shown in FIG. 3A, the energy of beta band signals (i.e., the signals within the frequency range of 20-40 Hz) is greatly enhanced in rats with Parkinson's disease. The upper diagram of FIG. 3A shows the amplitude of brainwave monitored by a neural-recording instrument (e.g., A-M Systems), and the amplitude is transformed into spectrogram through time-frequency analysis as shown in the lower diagram of FIG. 3A. The energy of beta band signals is shown in the spectrogram through black color with different shades of color. As shown in the lower diagram of FIG. 3A, a first scale 11 represents a high energy end while a second scale 12 represents a low energy end on the energy spectrum. In the spectrogram, beta oscillation is observed according to the high energy (i.e., the first scale 11) presence in the frequency range of 20-40 contrast, as shown in FIG. 3B, by subjecting STN to the stimulation with a frequency about 130 Hz, the energy present in the frequency range of 20-40 Hz is decreased compared to that shown in FIG. 3A. Accordingly, FIGS. 3A and 3B affirmatively show that the beta oscillations can be suppressed by STN stimulation.

In some embodiments, the stimulation is an electrical stimulation with a frequency higher than beta band. In some embodiments, the stimulation is an electrical stimulation with a frequency in the range from about 100 Hz to about 180 Hz. In some embodiments, the stimulation frequency is in the range from about 10 Hz to about 10K Hz. In some embodiments, the stimulation frequency depends on the demand of different types of treating purposes or clinical treating progress and thus not limited to the range as aforementioned.

In addition to the stimulation lead, the stimulation effect may be equivalent to providing some chemicals such as GABA (gamma-amino butyric acid) receptor antagonist directly injecting to the target layer of cortex. Referring to FIG. 4A, in the case of the beta oscillations are detected according to the brainwave of a rat with Parkinson's disease, after applying bicuculline, a GABA receptor antagonist, to Layers II and III of the motor cortex for five minutes, the brainwave recording is subsequently conducted and the result is shown in FIG. 4B. It can be observed in FIG. 4B that the energy present in the frequency range of 20-40 Hz is decreased and thus the beta oscillations are suppressed. Moreover, after twenty hours applying bicuculline, the GABA receptor antagonist, to Layers II and III of the motor cortex, the brainwave recording is subsequently conducted, and the result is shown in FIG. 4C. It can be observed in FIG. 4C that the energy present in the frequency range of 2.0-40 Hz may be detected again, indicating that another stimulation is necessary to be delivered.

Figure 5:
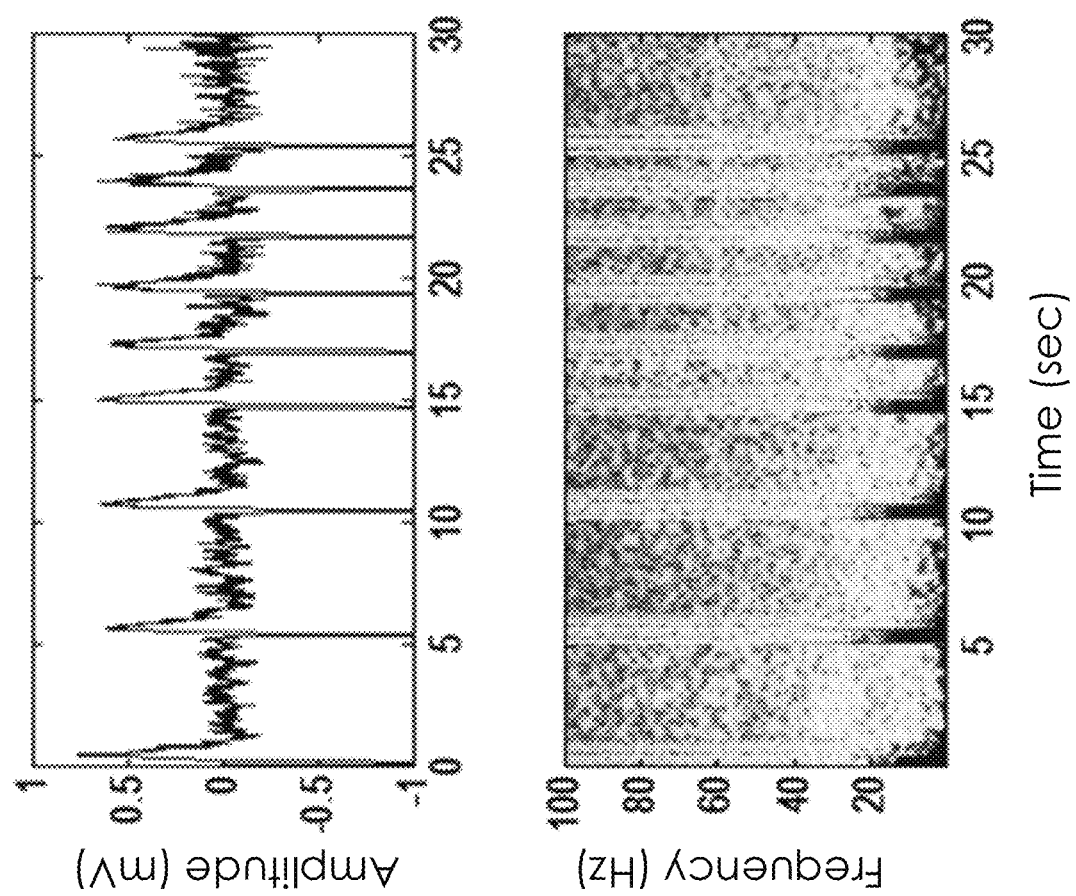
FIG. 5 illustrates the abnormal electrical activities presented by stimulating at Layer V of the cortex according to some embodiments of the present disclosure.

FIG. 5 is a comparative example showing that when the stimulation is delivered to an unsuitable layer of the cortex, a couple of side effects may occur such as synchronized neuron discharges, which is analogous to epilepsy. As shown in FIG. 5, after applying bicuculline to Layer V of the motor cortex for five minutes, signal in the frequency range of 20-40 Hz is decreased but synchronized neuron discharges are also presented (e.g., the spikes presented in amplitude domain and the spikes presented in frequency domain at approximately 1, 5, 10, 15, 17, 20, 22, 24 and 25 seconds). Comparing to the application of bicuculline to Layers II and III, it is proved that stimulation to a specific layer of the cortex may provide greater efficacy than other layers of the cortex.

In some comparative examples which cannot stimulate to a specific layer of the cortex, epidural electrical stimulation or intracortical electrical stimulation to cortex may both lead to side effect such as epilepsy. This is because epidural electrical stimulation may affect all layers of cortex, including the aforesaid specific layer (hereinafter "less preferred layer"). Therefore, in some embodiment, after determining which less preferred layer may induce such side effect, applying electrical, medical or other kinds of stimulations (e.g., by the functions of receptors as previously mentioned) to the layers other than the less preferred layer can effectively inhibit the beta oscillation of other kinds of abnormal electrical activities without generating unwanted side effect.

Moreover, Layer II is often grouped together with Layer III and referred to as Layer II/III. One of the reasons is that Layer II is thin (approximately 0.09-0.19 mm as aforementioned), so that in some embodiments, stimulation may be applied to Layer II and Layer III simultaneously. To be more detailed, the thickness of human cortex varies between about 1.59 and 3.01 mm, hence in some embodiments, the determination of stimulating layer/layers depends on the size of the target brain, the thickness of the target layers, and the area of the target cortex.

Figure 6:
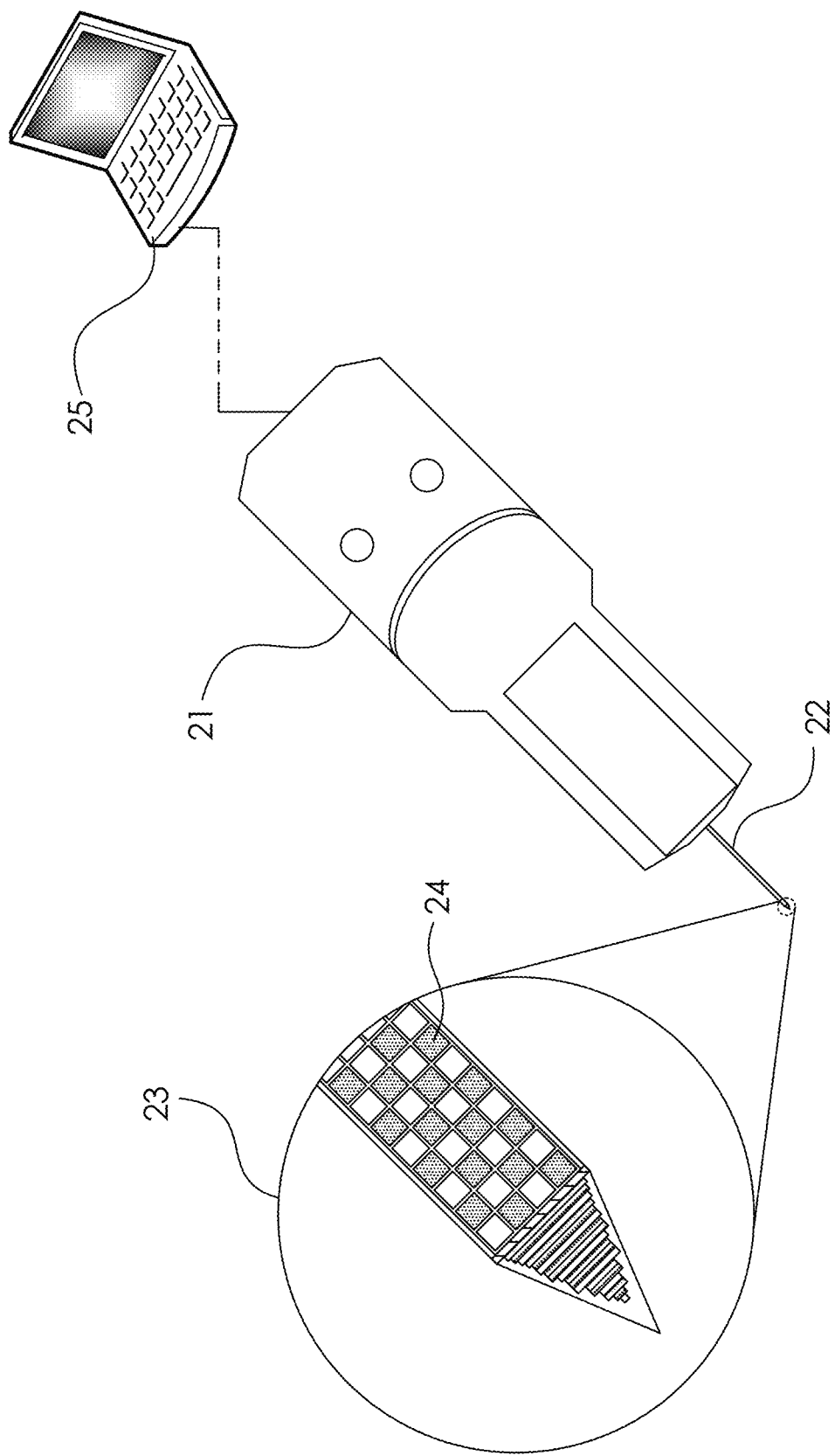
FIG. 6 illustrates the system for treating neural disorders according to some embodiments of the present disclosure.

Referring to FIG. 6, in some embodiments, the system for treating neural disorder includes a stimulation signal generator 21 and a layer-specific stimulation means 22. The layer-specific stimulation means 22 is coupled to the stimulation signal generator 21 and is configured to deliver at least a stimulation to a specific layer of a cortex of a patient with a neural disorder. In some embodiments, the layer-specific stimulation means 22 may be less than about 2 cm in length, or may be about 1 cm in length. In some embodiments, the layer-specific stimulation means 22 may be about 70 μm in width. In some embodiments, a stimulation electrode 23 can be disposed at an end of the layer-specific stimulation means 22. In some embodiments, the stimulation electrode 23 includes a plurality of stimulation sites 24. In some embodiments, each of the stimulation sites 24 is configured to deliver the stimulation to at least two specific layers of the cortex. The at least two specific layers of the cortex may be adjacent layers, for example, Layer II and Layer III, or may be non-adjacent layers, for example, Layer I and Layer IV. In some embodiments, each of the stimulation sites 24 is configured to deliver the stimulation to at least two sublayers of a specific layer of the cortex (as previously shown in FIG. 2), for example, Layer IIIA and Layer IIIB. In some embodiments, each of the stimulation sites 24 is configured to deliver the stimulation to a mixture of different specific layers of the cortex and different sublayers of a specific cortex.

In other words, the stimulation delivery in the present disclosure is meticulous in the controlling of the positions that effected by the stimulation. Accordingly, the stimulation electrode 23 is utilized to deliver the stimulation to the layers of the cortex, such as Layer I, Layer II, Layer III, etc., whereas the stimulation sites 24, which are the minimal stimulating units in some embodiments, may deliver the stimulations to the sublayers of the layer of the cortex. For example, the stimulation sites 24 may stimulate Layer IIIA (an upper portion of Layer III), Layer IIIB (a first middle portion of Layer III), Layer IIIC (a second middle portion of Layer III), Layer IIID (a lower portion of Layer III), etc., depending on the depth positions of the stimulation sites 24 in the layers of the cortex.

In some embodiments, a pair of the stimulation sites 24 may deliver the stimulations to a pairs of sublayers simultaneously, wherein one of the stimulation sites 24 may be utilized as a reference electrode. In some embodiments, the pair of the stimulation sites 24 may include an anode and a cathode. In some embodiments, the stimulations are delivered by two non-adjacent stimulation sites 24, for instance, referring to FIG. 7, Layer IIA (the upper portion of Layer II) and the Layer IIIA (the upper portion of Layer III) are stimulated simultaneously by the stimulation sites 24A and 24B, respectively, whereas the sublayers therebetween are precluded from direct stimulation. In some embodiments, the stimulations are delivered by more than two of the stimulation sites 24. In some embodiments, the stimulation may be delivered to at least two non-adjacent sublayers of the cortex simultaneously.

Again referring to FIG. 6, in some embodiments, the system further includes a recording instrument 25 coupled to the stimulation signal generator 21 and the layer-specific stimulation means 22. The recording instrument 25 may record a brainwave of the patient with a neural disorder for further analyzation. For example, the abnormal electrical signal or such as beta oscillation may be identified or recognized from the recorded brainwave and trigger the stimulation to the layers of the cortex. As aforementioned, the stimulation frequency depends on the demand of different types of treating purposes or clinical treating progress, and in order to satisfy such varieties of treating purposes or clinical treating progress, in some embodiment, the average durations, the intensities, or the ranges of the oscillations of each of the episodes of the abnormal electrical activities may be analyzed from the recorded brainwave, and be utilized for adjusting the parameters of the stimulation process. For instance, the stimulation may be adapted from a higher stimulation intensity to a lower stimulation intensity once the energy derived from an oscillation episode is measured to be half of its original value.

Furthermore, in the case of the stimulation electrode 23 delivers the stimulation to multiple layers of the cortex simultaneously (but still less than all of the layers of the cortex), the stimulation to each of the stimulated layer may be different, including in stimulation duration, stimulation intensity, stimulation frequency, frequency of stimulation, etc. Similarly, in the case of each of the stimulation sites 24 deliver the stimulation to the sublayers of a specific layers of the cortex simultaneously, the stimulation to each of the stimulated sublayers may be different, including in stimulation duration, stimulation intensity, stimulation frequency, frequency of stimulation, etc. In other words, the stimulation parameters applied to the layers or the sublayers may be mutually independent.

In one exemplary aspect, a method for treating neural disorders is provided. The method includes the following operation. A stimulation is delivered to a layer of a cortex of a patient with a neural disorder, wherein the stimulation is delivered to less than all layers of the cortex of the patient.

In another exemplary aspect, a method for treating neural disorders is provided. The method includes the following operation. A stimulation is delivered to a cortex of a patient with a neural disorder, wherein the stimulation delivered to one of a plurality of layers of the cortex is stronger than to other layers of the cortex.

In yet another exemplary aspect, a system for treating neural disorder is provided. The system includes a stimulation signal generator and a layer-specific stimulation means. The layer-specific stimulation means is coupled to the stimulation signal generator, configured to deliver a stimulation to a specific layer of a cortex of a patient with a neural disorder.

The foregoing outlines structures of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method for treating Parkinson's disease, comprising:
   implanting a stimulation lead to a cortex of a patient with Parkinson's disease,
   wherein the stimulation lead comprises an electrode having a plurality of stimulation sites arranged in an array along a length of the stimulation lead, and the stimulation lead is positioned in direct contact with a plurality of specific layers of the cortex through the plurality of stimulation sites,
wherein each of the plurality of stimulation sites is configured to deliver a stimulation to one of the specific layers of the cortex or a sublayer of one of the specific layers of the cortex in direct contact therewith, and
selectively delivering the stimulation to at least one of the specific layers of the cortex or the sublayer of one of the specific layers of the cortex of the patient with Parkinson's disease to suppress a pathological signature relating to Parkinson's disease, wherein the plurality of stimulation sites comprises a first stimulation site and a second stimulation site, and a parameter of a first stimulation delivered by the first stimulation site is different from a parameter of a second stimulation delivered by the second stimulation site,
wherein the specific layers of the cortex comprises molecular layer, external granular layer, external pyramidal layer, internal granular layer, internal pyramidal layer, and polymorphic layer.

2. The method of claim 1, wherein the cortex comprises motor cortex, somatosensory cortex, prefrontal cortex, and frontopolar cortex.

3. The method of claim 1, wherein the stimulation is an electrical stimulation with a frequency in the range of from about 100 Hz to about 180 Hz.

4. The method of claim 1, wherein the stimulation is an electrical stimulation with a frequency in the range of from about 10 Hz to about 10K Hz.

5. The method of claim 1, wherein the stimulation lead is electrically coupled to an electrical signal generator.

6. The method of claim 1, wherein the electrode is located at a distal end of the stimulation lead.

7. The method of claim 1, wherein a frequency of the stimulation is about 130 Hz.

8. The method of claim 1, wherein the pathological signature relating to Parkinson's disease is a beta oscillation of the cortex.

9. The method of claim 8, wherein a frequency of the stimulation is higher than a beta band of the beta oscillation of the cortex.

10. The method of claim 1, wherein the parameter comprises stimulation duration, stimulation intensity, stimulation frequency, and frequency of stimulation.

11. The method of claim 10, wherein the pathological signature relating to Parkinson's disease is a beta oscillation of the cortex, and further comprising adjusting the parameter in response to an analyzation result of the beta oscillation.

12. The method of claim 11, wherein the stimulation intensity is adjusted when an energy derived from an oscillation episode of the beta oscillation of the cortex is measured to be half of its original value.

13. The method of claim 1, further comprising:
determining a less preferred layer of the cortex; and
precluding from stimulating the less preferred layer while selectively delivering the stimulation to at least one of the specific layers of the cortex or the sublayer of one of the specific layers of the cortex, so as to avoid unwanted synchronized neuron discharges.

* * * * *